United States Patent [19]

Black

[11] 4,182,336
[45] Jan. 8, 1980

[54] SANITARY NAPKIN WITH ATTACHED DISPOSAL CONTAINER

[76] Inventor: Charles A. Black, 777 S. Lawrence St., Montgomery, Ala. 36101

[21] Appl. No.: 923,409

[22] Filed: Jul. 10, 1978

Related U.S. Application Data

[63] Continuation of Ser. No. 800,625, May 27, 1977, abandoned.

[51] Int. Cl.² ............................................. A61F 13/16
[52] U.S. Cl. ................................. 128/290 R; 206/438
[58] Field of Search ............... 206/438, 233, 494, 440; 128/290 R, 284, 287

[56] References Cited

U.S. PATENT DOCUMENTS

| 3,333,686 | 8/1967 | Schnabel | 206/233 |
| 3,604,423 | 9/1971 | Fraser | 128/290 R |
| 3,973,567 | 8/1976 | Srinidasan et al. | 128/290 R |

FOREIGN PATENT DOCUMENTS 868299  5/1961  United Kingdom ............... 128/290 R Primary Examiner—William T. Dixson, Jr.
Attorney, Agent, or Firm—Sherman & Shalloway

[57] ABSTRACT

Attached to the usual pad-type sanitary napkin is a sack-like container or bag made of thin, foldable, moisture-proof material. The bag is attached so that it may be opened to a position to receive the napkin. The bag with the napkin therein may then be closed for disposal.

1 Claim, 6 Drawing Figures

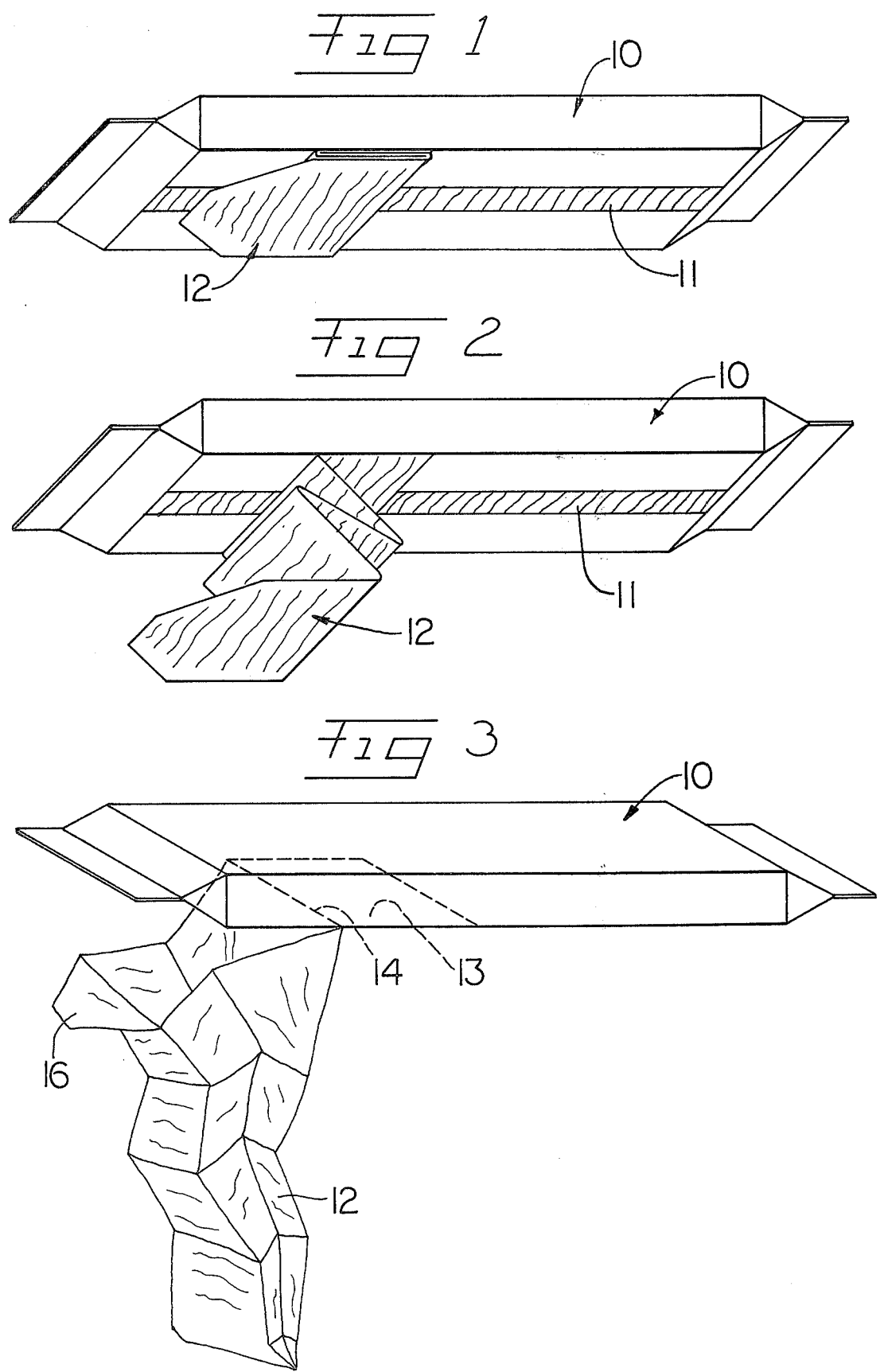

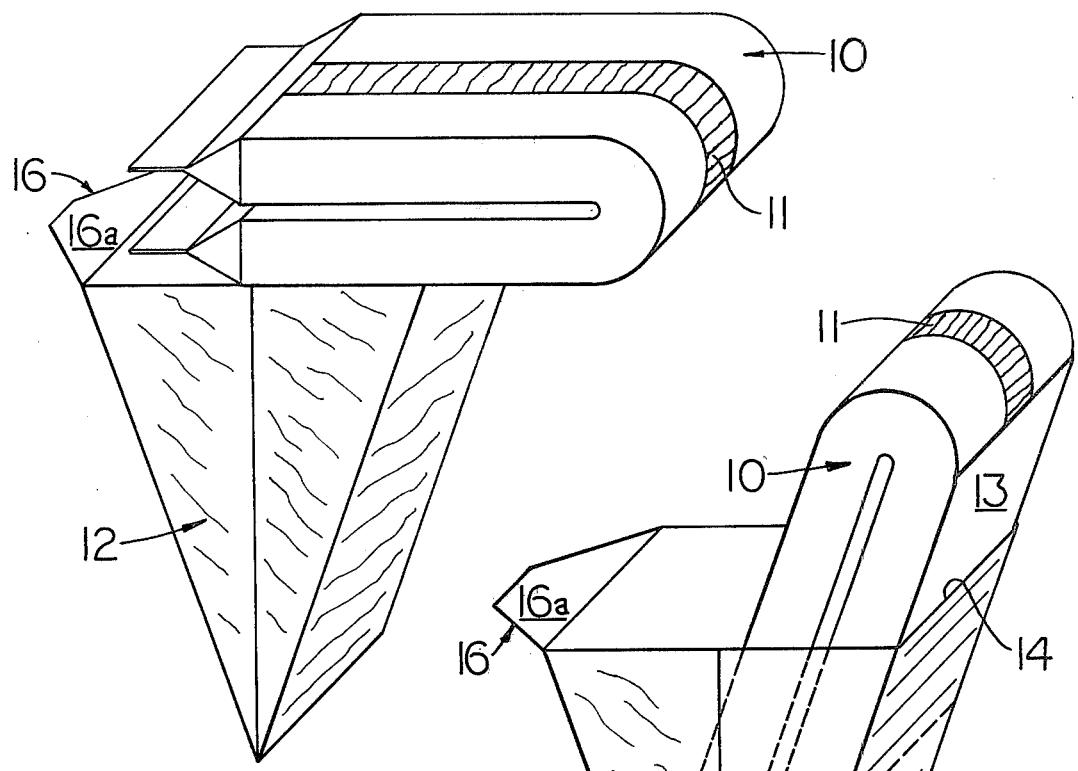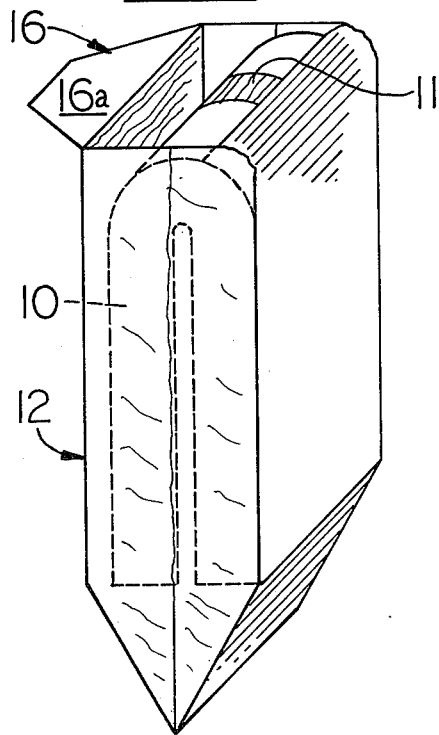

SANITARY NAPKIN WITH ATTACHED DISPOSAL CONTAINER

This is a continuation of application Ser. No. 800,625, filed May 27, 1977 now abandoned.

This invention relates to improvements in sanitary napkins and has for its object the provision of a sack-like container or bag carried by the napkin and in which the napkin may be placed for disposal.

A further object is to provide a napkin having affixed thereto a container of thin "plastic" material, substantially moisture-proof and which has an open mouth end, one wall of the container being elongated to provide a flap which may be attached to the napkin, whereby when desired the container may be unfolded, the napkin placed therein by a sort of folding and rolling action, thus to provide ready means for disposing of the napkin.

A sanitary napkin with attached container illustrating features of my invention is shown in the accompanying drawings forming a part of this application in which:

FIG. 1 is a view of the napkin with the container in folded position;

FIG. 2 is a view with the container partly unfolded;

FIG. 3 is a view with the container fully unfolded;

FIG. 4 is a view showing the initial stage of inserting the folded sanitary napkin into the container;

FIG. 5 is a view showing an intermediate state in the insertion of the napkin; and, FIG. 6 is a view showing the napkin fully inserted in the container, with the sealing flap ready to be closed.

Referring now to the drawings for a better understanding of my invention I show at 10 the usual pad-type sanitary napkin. As is understood, this napkin is provided on the surface opposite that to be placed against the body with a line or strip of adhesive material 11 as to adhere to an undergarment, thus to aid in holding the pad in place.

My invention comprises the attachment to the napkin of a sack-like container indicated generally by the numeral 12. The container may be made of thin, substantially moisture-proof, or plastic material of a thickness so as to be readily foldable to the position shown in FIG. 1, whereby the same is compact enough not to interfere with the normal use of the sanitary napkin.

As shown in the drawings, the container is provided with a flap 13 which extends past the mouth or upper wall of the container. This flap is preferably secured to the napkin by adhesive, whereby the entire body of the sack is hinged to the napkin around the hinge line 14, this line being located adjacent the upper end of the mouth of the sack.

The opposite or front wall of the sack may be provided with a flap 16 which may carry adhesive if desired.

In use it will be seen that when it is desired to dispose of the napkin the series of steps as shown in FIGS. 1 to 6 is followed. This, the sack or container if first unfolded to the position of FIG. 3. The sanitary napkin is now doubled on itself as shown in FIG. 4. With the sack held open by grasping the tab 16 between the thumb and forefinger of one hand the napkin is rolled into position simply by bringing the free or unfolded ends of the pad around and down into the sack. Finally, the napkin is pushed from the position of FIG. 5 to the position of FIG. 6 wherein it is substantially fully enclosed in the container. The flap 16 may now be folded over from left to right as shown in FIG. 6 thus substantially to close the container with the napkin in place therein. As stated, the surface $16^a$ of the tab 16 may be coated with adhesive if desired. However, it may be that in some instances the adhesive in the band 11 which is still exposed as shown in FIG. 6 may be sufficient to hold the flap 16 in place. In any event, the bag can be closed by any suitable form of adhesive whether on the flap $16^a$ or otherwise.

In view of the foregoing it will be seen that I have invented an improved, entirely practical and satisfactory means of disposing of sanitary napkins which means comprises essentially a foldable, sack-like container carried by the napkin.

While I have shown my invention in but one form, it will be obvious to those skilled in the art that it is not so limited but is susceptible of various changes and modifications without departing from the spirit thereof.

What I claim is:

1. As an article of manufacture,
    (a) a sanitary napkin having secured thereto a sack for disposing of the napkin,
    (b) said sack being made of foldable, substantially moisture-proof material,
    (c) said sack being generally triangular when in open position and as viewed in side elevation,
    (d) there being a first flap extension on a rear wall of the sack at its open end and extending outwardly of its open end, said flap extension being secured to the surface of the napkin on the side thereof opposite the side disposed to contact the user's body and at a position intermediate one end of the napkin and a folding zone thereof, whereby the sack may be opened by unfolding the same, the napkin folded once upon itself and inserted directly into the sack with its free ends adjacent the bottom of the sack and the reaminder thereof and the first flap extension being received within the sack away from the open end of the sack,
    (e) a second flap extension on said sack on the front wall thereof and adjacent the open end of the sack and adapted to reach across the open end of the sack to close the same, and
    (f) means to secure the second flap to the rear wall of the sack, thus to close the sack with the napkin and the first flap in place therein.

* * * * *